(12) United States Patent
Mori

(10) Patent No.: US 12,311,094 B2
(45) Date of Patent: May 27, 2025

(54) SENSOR SYSTEM AND MEDICAL DEVICE

(71) Applicant: TERUMO KABUSHIKI KAISHA, Tokyo (JP)

(72) Inventor: Takehisa Mori, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 739 days.

(21) Appl. No.: 17/400,558

(22) Filed: Aug. 12, 2021

(65) Prior Publication Data

US 2021/0369935 A1    Dec. 2, 2021

Related U.S. Application Data

(63) Continuation of application No. PCT/JP2020/005753, filed on Feb. 14, 2020.

(30) Foreign Application Priority Data

Mar. 7, 2019 (JP) .................. 2019-041317

(51) Int. Cl.
*A61M 1/36* (2006.01)
(52) U.S. Cl.
CPC ........ *A61M 1/3663* (2013.01); *A61M 1/3639* (2013.01); *A61M 2205/3317* (2013.01); *A61M 2205/3331* (2013.01)
(58) Field of Classification Search
CPC .............. A61M 1/3663; A61M 1/3639; A61M 2205/3317; A61M 2205/3331
See application file for complete search history.

(56) References Cited

U.S. PATENT DOCUMENTS

| | | | |
|---|---|---|---|
| 10,226,193 B2 | 3/2019 | Jacobsen | |
| 2007/0179433 A1* | 8/2007 | Jonsson | A61M 1/3639 604/4.01 |
| 2013/0303967 A1 | 11/2013 | Utz et al. | |
| 2014/0243703 A1* | 8/2014 | Schmidt | A61B 5/031 600/561 |
| 2014/0276346 A1 | 9/2014 | Sadanand | |
| 2017/0074695 A1* | 3/2017 | Baecke | G01L 19/0038 |
| 2019/0011321 A1* | 1/2019 | Kobayashi | G01L 19/003 |

FOREIGN PATENT DOCUMENTS

JP    3-46729 Y    10/1991

OTHER PUBLICATIONS

International Search Report, PCT/JP2020/005753, Feb. 3, 2020.
Written Opinion of the International Search Authority, PCT/JP2020/005753, Oct. 3, 2020.

* cited by examiner

*Primary Examiner* — Susan S Su
*Assistant Examiner* — Erin A Kim
(74) *Attorney, Agent, or Firm* — MacMillan, Sobanski & Todd, LLC

(57) ABSTRACT

A sensor system (10) has a medical device provided with a first transmission/reception unit (16) installed inside a medical instrument (12) to output a detection signal of a sensor unit (22), and a second transmission/reception unit (18) detachably installed outside the medical instrument (12) to transmit/receive a signal to and from the first transmission/reception unit (16) in a contactless manner. The first transmission/reception unit (16) and the second transmission/reception unit (18) are arranged so as to be opposed to each other across the medical instrument (12) to transmit/receive the signal by electromagnetic induction.

11 Claims, 5 Drawing Sheets

SENSOR SYSTEM AND MEDICAL DEVICE

CROSS REFERENCE TO RELATED APPLICATIONS

This application is a continuation of PCT Application No. PCT/JP2020/005753, filed Feb. 14, 2020, based on and claiming priority to Japanese Application No. 2019-041317, filed Mar. 7, 2019, both of which are incorporated herein by reference in their entirety.

BACKGROUND OF THE INVENTION

The present invention relates to a sensor system attached to a medical instrument including a blood flow path and a medical device.

Conventionally, disposable medical instruments including a blood pump, a blood flow path, and an artificial lung have been used in a medical setting. High reliability is required in these medical instruments, and it is desired to detect an abnormality in the blood flow path due to occurrence of thrombus and the like at an early stage to prevent a trouble. As a method of detecting the abnormality in the blood flow path, a technology of detecting a pressure in the blood flow path is known.

For example, U.S. Pat. No. 10,226,193B2 discloses providing a wireless pressure sensor in a catheter inserted into a subject's body.

As in the above-described conventional technology, the pressure may be easily detected by arranging a pressure sensor at a desired site. However, in the above-described wireless sensor, it is necessary to extend wiring for power supply to the wireless sensor. It is necessary to pull wiring out of the blood flow path also in a case of using a wired pressure sensor.

Such wiring might interfere with handling of a medical device in a medical setting. There also is a problem that it is difficult to secure electrical safety because the wiring is arranged in a portion adjacent to the blood.

Therefore, a sensor system and a medical device excellent in electrical safety and handleability are desired.

SUMMARY OF THE INVENTION

One aspect of the following disclosure is a sensor system provided with a first transmission/reception unit installed inside a medical instrument which outputs a detection signal comprising measurement data of a sensor unit, and a second transmission/reception unit adapted to selectably attach on an outside surface of the medical instrument which transmits/receives a signal to and from the first transmission/reception unit in a contactless manner, in which the first transmission/reception unit and the second transmission/reception unit are arranged so as to be opposed to each other across the medical instrument in order to transmit/receive the signal by electromagnetic induction.

Another aspect of the following disclosure is a medical device provided with a medical instrument including a blood flow path, and a sensor system provided with a first transmission/reception unit incorporated inside the medical instrument for exposure to the blood flow path of the medical instrument in order to output a detection signal of a sensor unit, and a second transmission/reception unit detachably installed outside the medical instrument which transmits/receives a signal to and from the first transmission/reception unit in a contactless manner, in which the first transmission/reception unit and the second transmission/reception unit are arranged so as to be opposed to each other across the medical instrument in order to transmit/receive the signal by electromagnetic induction.

According to the sensor system and medical device of the above-described aspects, the first transmission/reception unit installed in the blood flow path and the second transmission/reception unit outside are connected to each other by electromagnetic induction in a contactless manner, so that electrical safety may be achieved. Since the second transmission/reception unit may be unattached in a case where it is not required to measure, the wiring is simplified and handleability of the medical device is improved.

DETAILED DESCRIPTION OF PREFERRED EMBODIMENTS

Preferred embodiments of the present invention are hereinafter described in detail with reference to the accompanying drawings.

A sensor system 10 according to this embodiment is attached to a blood flow path 14 of a disposable medical device such as an artificial lung and a dialysis device, and may be used for detecting an abnormality of the medical device.

Figure 1:
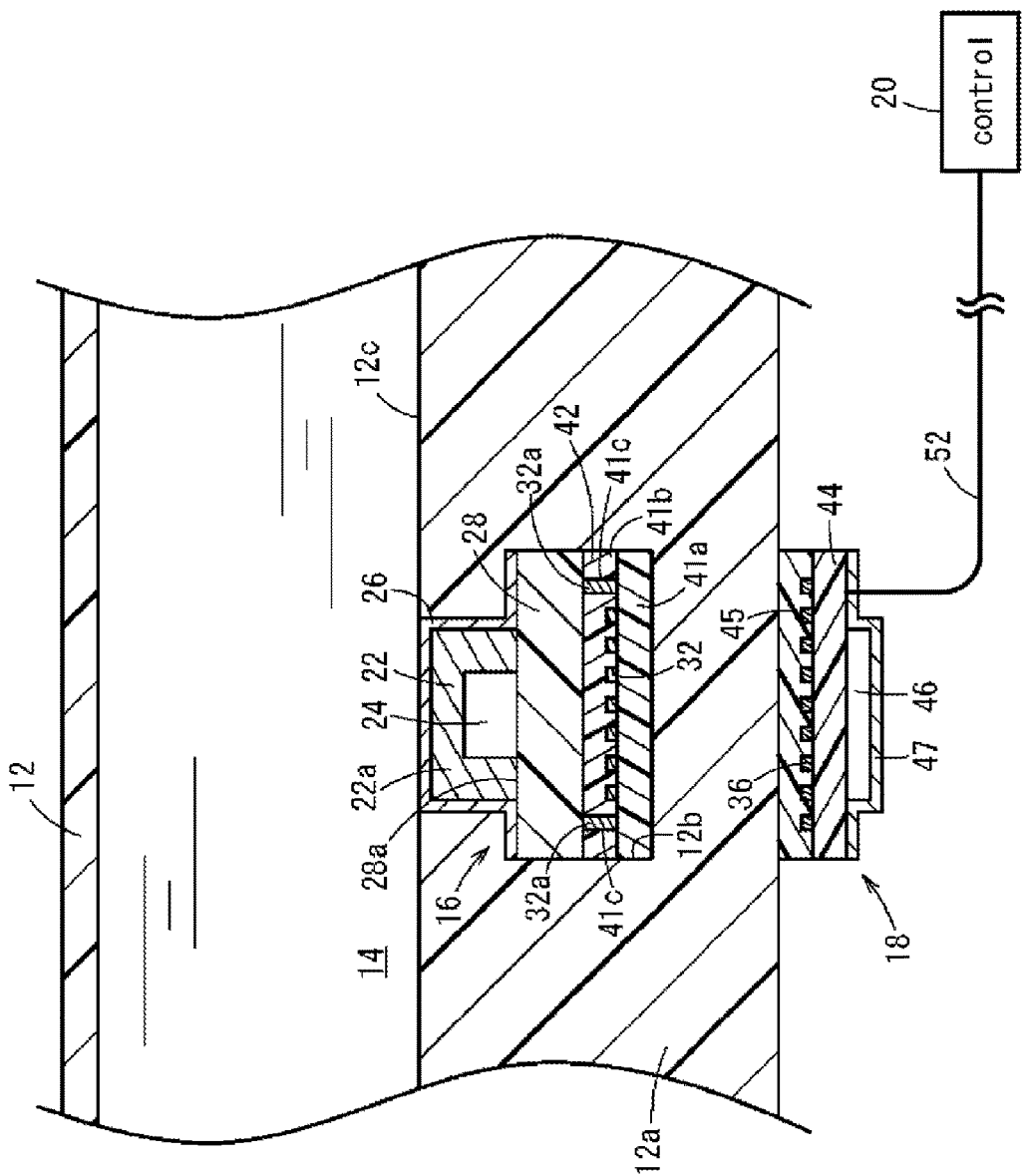
FIG. 1 is a cross-sectional view of a sensor system according to an embodiment.

As illustrated in FIG. 1, the sensor system 10 is provided with a first transmission/reception unit 16 provided inside a medical instrument 12 including the blood flow path 14, and a second transmission/reception unit 18 attached onto an outside surface of the medical instrument 12. The first transmission/reception unit 16 and the second transmission/reception unit 18 are configured to supply power and transmit/receive signals in a contactless manner without wiring between them.

The first transmission/reception unit 16 is provided with a sensor unit 22, a semiconductor substrate 28, and a substrate with built-in coil 42. The sensor unit 22 is provided with a piezoresistance semiconductor pressure sensor 22a with a cavity 24 inside, the cavity 24 kept in a vacuum state and capable of detecting an absolute pressure. As a result, it is possible to eliminate the necessity of calibration work in each measurement. The sensor unit 22 is such that an upper end portion is distorted toward the cavity 24 according to a pressure difference between the cavity 24 and the outside, thereby indicating a change in resistance value according to an external pressure (e.g., a pressure present within blood flow path 14). The sensor unit 22 is further provided with a sensor amplifier that converts a resistance change of the piezoresistance semiconductor pressure sensor 22a into a voltage value to output. The sensor unit 22 including the sensor amplifier and the piezoresistance semiconductor pressure sensor 22a is joined to a principal surface 28a (upper surface) of the semiconductor substrate 28. The sensor unit 22 and the semiconductor substrate 28 are covered with a protective layer 26 made of resin and the like.

Figure 2:
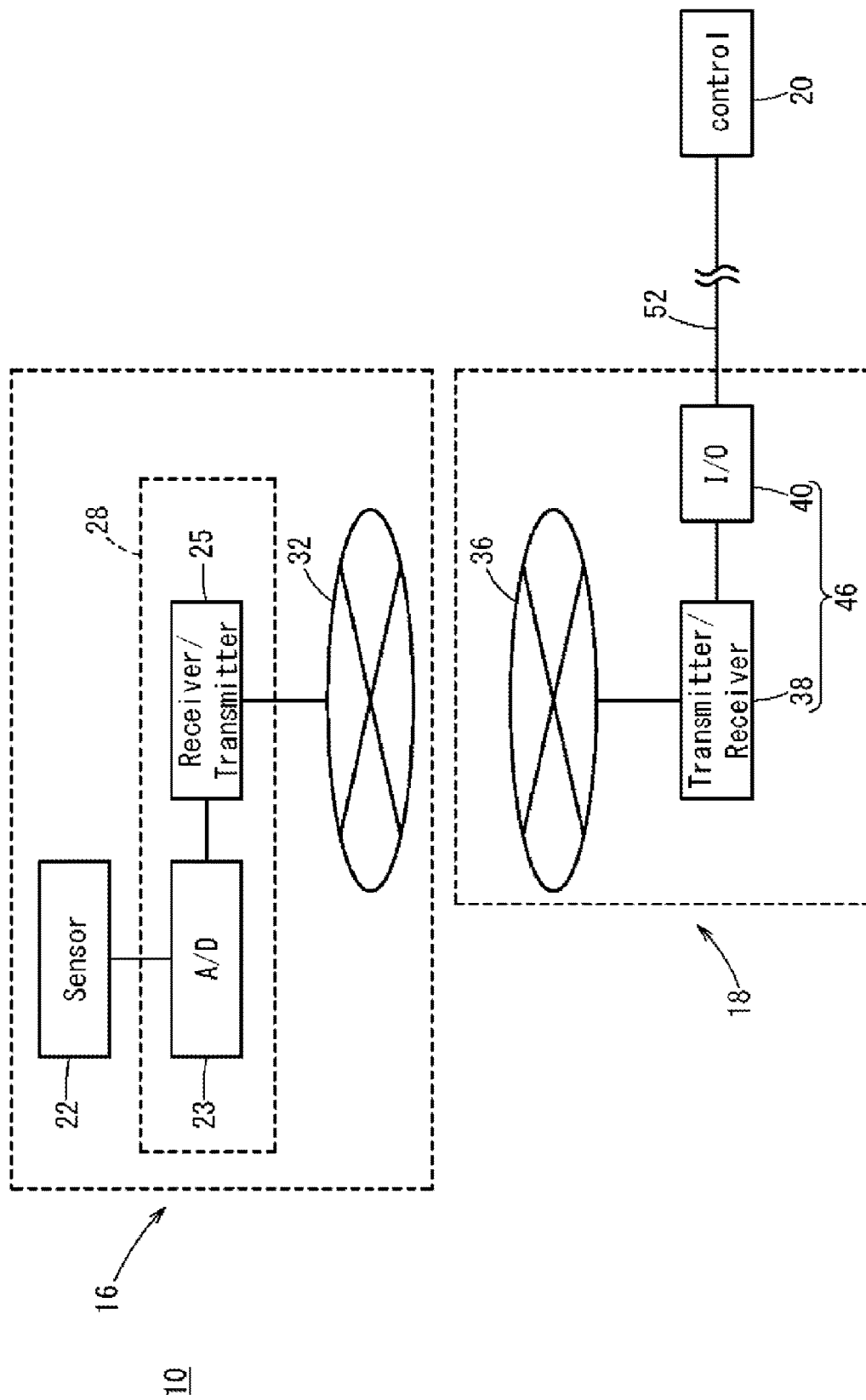
FIG. 2 is a block diagram of the sensor system in FIG. 1.

As illustrated in FIG. 2, an A/D converter 23 and a transmission/reception circuit 25 are formed on the semiconductor substrate 28. The A/D converter 23 is electrically connected to the sensor unit 22 and the transmission/reception circuit 25, converts an output voltage of the sensor amplifier of the sensor unit 22 into a digital signal, and outputs the same to the transmission/reception circuit 25. The transmission/reception circuit 25 is electrically connected to a first coil 32. The transmission/reception circuit 25 converts electric power supplied via the first coil 32 into a predetermined voltage and supplies the same to the sensor unit 22 and the A/D converter 23. The transmission/reception circuit 25 also modulates the digital signal received from the A/D converter 23 into a signal of a predetermined frequency, and transmits the same to the second transmission/reception unit 18 via the first coil 32. The A/D converter 23 and the transmission/reception circuit 25 are formed on the principal surface 28a (upper surface) or a lower surface of the semiconductor substrate 28 by a semiconductor manufacturing process.

As illustrated in FIG. 1, the substrate with built-in coil 42 is joined to the lower surface side of the semiconductor substrate 28. The substrate with built-in coil 42 is formed of a multilayer substrate in which a plurality of resin layers 41a and 41b is stacked, and the first coil 32 formed into a planar shape is embedded between the resin layers 41a and 41b. That is, the first coil 32 is formed flat in a direction parallel to principal surfaces of the semiconductor substrate 28 and the substrate with built-in coil 42, and a winding axis of the first coil 32 is in a direction perpendicular to the semiconductor substrate 28 and the substrate with built-in coil 42. The first coil 32 is formed on the resin layer 41a, for example, as a spiral conductor pattern.

The substrate with built-in coil 42 including the first coil 32 is manufactured by, for example, a build-up (deposition) method and the like. A via hole 41c that penetrates the resin layer 41b in a thickness direction is formed at one end and the other end of the first coil 32. A conductor 32a such as copper is embedded in the via hole 41c. The first coil 32 is electrically connected to the semiconductor substrate 28 via the conductor 32a embedded in the via hole 41c.

The first transmission/reception unit 16 is arranged so that the sensor unit 22 is adjacent to the blood flow path 14. In this embodiment, as illustrated in the drawing, the first transmission/reception unit 16 is accommodated in a recess 12b formed on a side wall 12a of the medical instrument 12 (e.g., a flexible tube forming part of an extracorporeal circulation system) including the blood flow path 14. Note that, from the viewpoint of preventing occurrence of thrombus, the first transmission/reception unit 16 is preferably attached inside the medical instrument 12 so as not to protrude from (e.g., is flush with) an inner wall 12c of the medical instrument 12. That is, this is preferably arranged so that an upper end of the sensor unit 22 of the first transmission/reception unit 16 is flush with the inner wall 12c of a lumen or channel conveying blood through the medical instrument 12.

In the first transmission/reception unit 16 described above, the substrate with built-in coil 42 may be formed into a rectangular shape of, for example, about 2 mm square to 5 mm square. The larger an area of the substrate with built-in coil 42, then the larger an area of the first coil 32 can be, so that power can be supplied more easily and efficiently from the second transmission/reception unit 18 to transmission/reception unit 16. The semiconductor substrate 28 can have a size equivalent to or smaller than that of the substrate with built-in coil 42.

The second transmission/reception unit 18 is provided with a second coil 36, a coil substrate 44, a circuit element 46, and connection wiring 52. The coil substrate 44 is a substrate made of a resin alone or a fiber reinforced resin, or ceramics, on one surface of which the second coil 36 planarly wound as a spiral pattern is formed. The second coil 36 is planarly formed along a principal surface of the coil substrate 44, and a winding axis thereof is in a direction perpendicular to the coil substrate 44. The second coil 36 and the coil substrate 44 are covered with a coating resin 45.

The circuit element 46 is mounted on the other surface of the coil substrate 44. As illustrated in FIG. 2, the circuit element 46 is provided with a transmission/reception circuit 38 and an input/output unit 40. The transmission/reception circuit 38 is electrically connected to the second coil 36, supplies electric power for driving the second coil 36, and receives a detection signal of the first transmission/reception unit 16 via the second coil 36. The input/output unit 40 is connected to a control device 20 via the connection wiring 52. The input/output unit 40 is configured to receive a control signal from the control device 20 and to transmit measurement data of the first transmission/reception unit 16 to the control device 20.

The transmission/reception circuit 38 and the input/output unit 40 of the circuit element 46 may be formed on the same semiconductor chip, or formed on different semiconductor chips to be electrically connected on the coil substrate 44. Lower surfaces of the circuit element 46 and the coil substrate 44 are covered with a resin layer 47.

The connection wiring 52 includes a plurality of conductor wires and supplies electric power required for an operation of the second transmission/reception unit 18. The connection wiring 52 is configured to transmit a signal between the control device 20 and the second transmission/reception unit 18.

The second transmission/reception unit 18 described above is detachably arranged in a direction in which the second coil 36 is parallel to the first coil 32, in a position in which the second coil 36 is opposed to the first coil 32 (e.g., first coil 32 and second coil 36 are facing each other and are electromagnetically coupled across a small gap). Note that, the direction in which the second coil 36 is parallel to the first coil 32 is not limited to the direction in which the second coil 36 is strictly parallel to the first coil 32, but also includes a case where the second coil 36 is slightly inclined with respect to the first coil 32. That is, the second coil 36 may be inclined within a range in which the first coil 32 continues to generate sufficient electric power as required for an operation of the first transmission/reception unit 16.

An operation of the sensor system 10 is described below.

Figure 3:
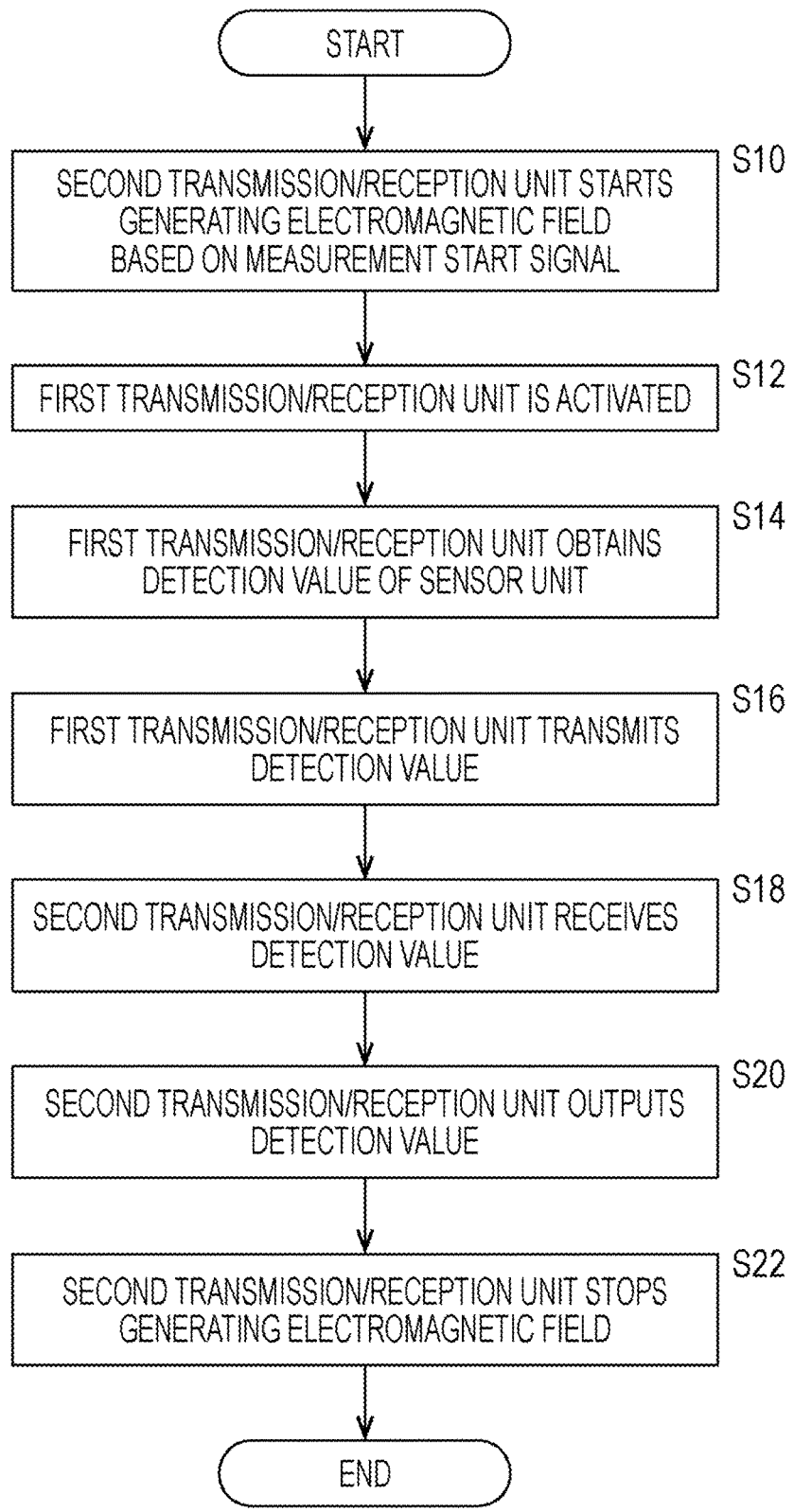
FIG. 3 is a flowchart illustrating an operation of the sensor system in FIG. 1.

The sensor system 10 operates so as to detect a pressure of the blood flow path 14 of the medical instrument 12 at a predetermined sampling frequency. The sampling frequency may be set to, for example, 10 Hz. As illustrated in FIG. 3, first, at step S10, the second transmission/reception unit 18 starts generating an electromagnetic field based on a measurement start signal. Here, the measurement start signal is transmitted from the control device 20 to the second transmission/reception unit 18 via the connection wiring 52 every sampling cycle.

When receiving the measurement start signal via the input/output unit 40, the transmission/reception circuit 38 supplies an alternating current of a predetermined frequency to the second coil 36 to generate the electromagnetic field of a predetermined frequency from the second coil 36. Although not especially limited, the frequency of the electromagnetic field generated by the second coil 36 may be set to, for example, about 135 kHz. The second coil 36 continuously generates the electromagnetic field until the reception of the measurement start signal from the second transmission/reception unit 18 terminates.

Figure 4:
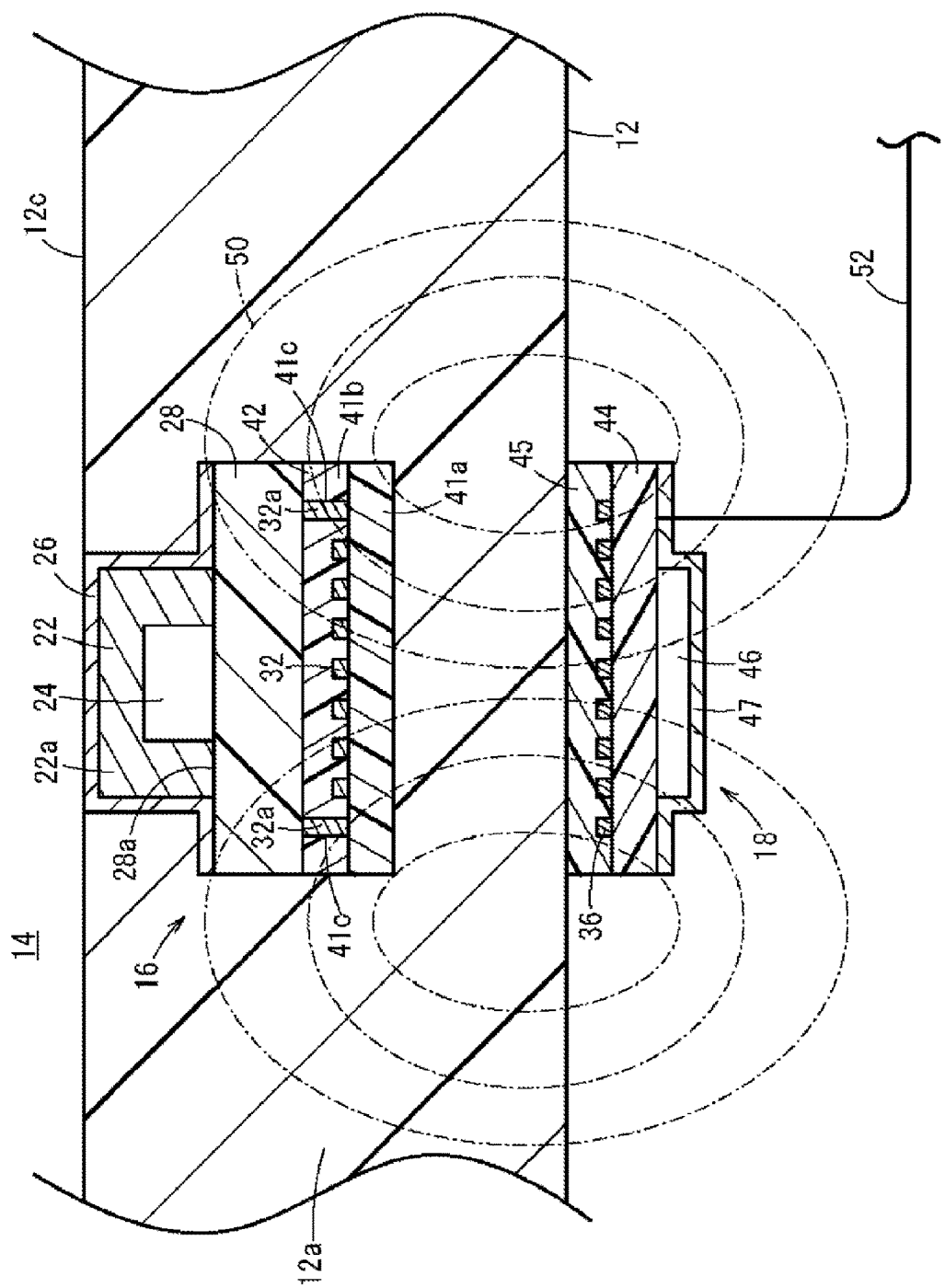
FIG. 4 is a cross-sectional view illustrating a connection state of a first transmission/reception unit and a second transmission/reception unit of the sensor system in FIG. 1.

Next, at step S12, the first transmission/reception unit 16 receives the electromagnetic field of the second coil 36 to be activated. As illustrated in FIG. 4, a magnetic flux 50 is generated around the second coil 36 by the alternating current flowing in the second coil 36. An alternating current is generated in the first coil 32 by electromagnetic induction via the magnetic flux 50. The alternating current generated in the first coil 32 is converted into DC power of a predetermined voltage by the transmission/reception circuit 25 provided on the semiconductor substrate 28, and the electric power is supplied to the A/D converter 23 and the sensor unit 22. As a result, the first transmission/reception unit 16 is activated.

Next, at step S14 in FIG. 3, the first transmission/reception unit 16 obtains a detection value of the sensor unit 22. That is, the sensor unit 22 outputs a voltage value corresponding to a pressure difference between the piezoresistance semiconductor pressure sensor 22a and the cavity 24 to the A/D converter 23. The A/D converter 23 converts the output voltage of the sensor unit 22 into the digital signal and transmits the same to the transmission/reception circuit 25.

Next, at step S16, the first transmission/reception unit 16 transmits the detection value of the sensor unit 22. That is, the transmission/reception circuit 25 of the first transmission/reception unit 16 modulates the digital signal to a predetermined frequency and transmits the same from the first coil 32.

Next, at step S18, the second transmission/reception unit 18 receives the detection value of the sensor unit 22. A transmission signal of the first transmission/reception unit 16 is received by the transmission/reception circuit 38 of the second transmission/reception unit 18 via the second coil 36 by electromagnetic induction.

Next, at step S20, the second transmission/reception unit 18 outputs the detection value of the sensor unit 22 to the control device 20. That is, the detection signal received by the transmission/reception circuit 38 is input to the input/output unit 40, converted into a predetermined data format, and then transmitted to the control device 20 via the connection wiring 52.

After that, at step S22, the second transmission/reception unit 18 stops generating the electromagnetic field via the second coil 36. As described above, the operation of the sensor system 10 in one sampling is completed. The sensor system 10 repeatedly performs the operation at steps S10 to S22 described above every sampling cycle.

Figure 5A:
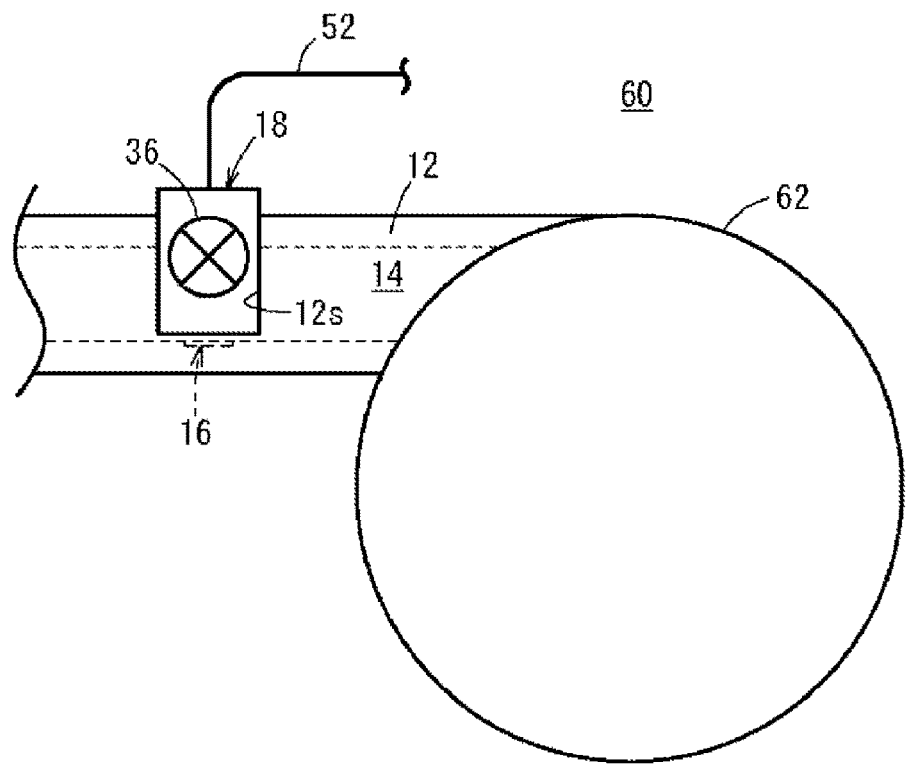
FIG. 5A is a plan view illustrating a configuration example of a medical device provided with the sensor system in FIG. 1.

As illustrated in FIG. 5A, the sensor system 10 may be used in a medical device 60. The medical device 60 is provided with a blood pump 62 and the medical instrument 12 (e.g., tube for conveying blood) connected to an inlet or outlet of the blood pump 62. The first transmission/reception unit 16 is provided inside the medical instrument 12 (tube). The second transmission/reception unit 18 is detachably attached to the outside surface of the medical instrument 12 (tube). The medical instrument 12 (tube) is provided with a guide feature 12s formed as a groove or a recess on the outside surface for attaching the second transmission/reception unit 18 in a predetermined position. As illustrated in FIG. 5A, by attaching the second transmission/reception unit 18 to the guide feature 12s, an inner pressure of the medical device 60 may be measured.

Figure 5B:
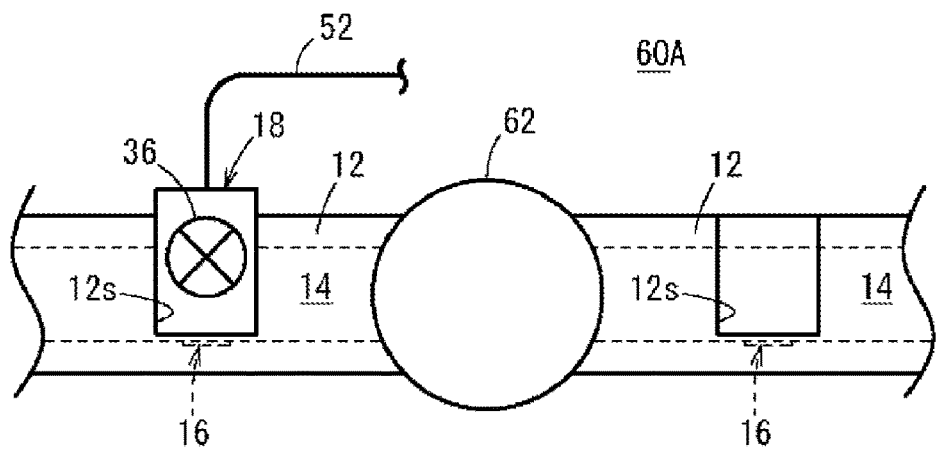
FIG. 5B is a plan view illustrating another configuration example of the medical device provided with the sensor system in FIG. 1.

As illustrated in FIG. 5B, in a medical device 60A, the medical instrument 12 (tube) includes respective sections connected to the inlet and the outlet of the blood pump 62. A respective first transmission/reception unit 16 is provided inside each of the separate sections of medical instrument 12 (tube). In such an embodiment, in the event that it is not required to measure a pressure at a plurality of sites on the same blood flow path 14, a second transmission/reception unit 18 is attached to only one of the first transmission/reception units 16. In this manner, since it is possible to attach the second transmission/reception unit 18 only to a necessary portion, the connection wiring 52 may be minimized. Therefore, in the medical device 60A, the connection wiring 52 is simplified and handleability in a medical setting is improved.

The sensor system 10 and the medical devices 60 and 60A of this embodiment have the following effects.

The sensor system 10 is provided with the first transmission/reception unit 16 incorporated inside the medical instrument 12 (e.g., embedded in a tube or other body conveying a flow of blood) to output the detection signal of the sensor unit 22, and the second transmission/reception unit 18 detachably installed outside the medical instrument 12 to transmit/receive the signal to and from the first transmission/reception unit 16 in a contactless manner, in which the first transmission/reception unit 16 and the second transmission/reception unit 18 are arranged so as to be opposed to each other across the medical instrument 12 to transmit/receive the signal by electromagnetic induction. The first transmission/reception unit 16 provided so as to face the blood flow path 14 and the second transmission/reception unit 18 attached outside the medical instrument 12 are connected to each other in a contactless manner by electromagnetic induction. As a result, electrical safety of the medical device 60 may be achieved.

In the above-described sensor system 10, the first transmission/reception unit 16 is provided with the semiconductor substrate 28 (substrate), the sensor unit 22 mounted on the semiconductor substrate 28 and arranged at a site in contact with the blood flow path 14 of the medical instrument 12 including the blood flow path 14, and the first coil 32 wound in the direction parallel to the principal surface 28a of the semiconductor substrate 28. With this configuration, the first transmission/reception unit 16 may be made thinner and smaller. As a result, the first transmission/reception unit 16 may also be provided inside a narrow medical instrument 12 such as a tube.

In the above-described sensor system 10, the second transmission/reception unit 18 includes the planarly wound second coil 36, and the first transmission/reception unit 16 and the second transmission/reception unit 18 are arranged so as to be opposed to each other so that the winding axis of the first coil 32 is parallel to the winding axis of the second coil 36. This facilitates electromagnetic induction between the first coil 32 and the second coil 36.

In the above-described sensor system 10, the second transmission/reception unit 18 may supply drive power to the first transmission/reception unit 16 by current induction. As a result, it becomes possible to operate the first transmission/reception unit 16 without providing a storage battery and power supply wiring on the first transmission/reception unit 16.

In the above-described sensor system 10, the first transmission/reception unit 16 may be configured to transmit the detection signal of the sensor unit 22 to the second transmission/reception unit 18 by electromagnetic induction. With this configuration, a device configuration may be made simple and the second transmission/reception unit 18 may be made smaller.

In the above-described sensor system 10, the sensor unit 22 may be the piezoresistance semiconductor pressure sensor 22a (pressure sensor) that detects a pressure of the blood flowing in the blood flow path 14. As a result, it is possible to detect an abnormality due to obstruction of the blood flow path 14 and the like.

In the above-described sensor system 10, the guide feature 12s that indicates an installation position of the first transmission/reception unit 16 and facilitates optional attachment of a second transmission/reception unit 18 in proper alignment may be provided on an outside surface of the medical instrument 12. With this configuration, the second transmission/reception unit 18 may be attached in an appropriate position.

In the above-described sensor system 10, the first transmission/reception unit 16 may be attached inside the medical instrument 12 so that the upper end portion thereof is flush with the inner wall 12c of the blood flow path 14 (such that the upper end portion does not protrude from the inner wall 12c). This makes it possible to prevent occurrence of thrombus in the blood flow path 14.

The above-described medical devices 60 and 60A are provided with the sensor system 10 provided with the medical instrument 12 including the blood flow path 14, the first transmission/reception unit 16 installed inside the blood flow path 14 of the medical instrument 12 to output the detection signal of the sensor unit 22, and the second transmission/reception unit 18 detachably installed outside the medical instrument 12 to transmit/receive the signal to and from the first transmission/reception unit 16 in a contactless manner, in which the first transmission/reception unit 16 and the second transmission/reception unit 18 are arranged so as to be opposed to each other across the medical instrument 12 to transmit/receive the signal by electromagnetic induction. As a result, electrical safety of the medical devices 60 and 60A is achieved. Since the second transmission/reception unit 18 can be left in a detached condition in a case where it is not required to measure, the connection wiring 52 is simplified and handleability of the medical devices 60 and 60A is improved.

The sensor system and the medical device are described above with reference to the preferable embodiment, but the sensor system and the medical device are not limited to the above-described embodiment, and it goes without saying that various modifications may be made without departing from the gist of the present invention. For example, the pressure sensor using the piezoresistance semiconductor pressure sensor 22a is described as an example of the sensor unit 22, but there is no limitation. The sensor unit 22 may be a temperature sensor that detects temperature of the blood, or may include an electrochemical sensor that detects a predetermined blood component by an electrochemical reaction with the blood. The sensor unit 22 may also be a sensor that detects various characteristics such as magnetic characteristics, optical characteristics, and viscosity of the blood.

What is claimed is:

1. A sensor system for a medical instrument having a flexible tube for conveying a blood flow path, comprising:
    a first transmission/reception unit incorporated inside the medical instrument and configured to output a detection signal comprising measurement data; and
    a second transmission/reception unit adapted to detachably install to an outside surface of the medical instrument to transmit/receive signals to and from the first transmission/reception unit in a contactless manner;
    wherein the first transmission/reception unit and the second transmission/reception unit are arranged so as to be opposed to each other across the medical instrument and transmit/receive the signals by electromagnetic induction;
    wherein the first transmission/reception unit comprises:
        a substrate;
        a sensor unit mounted on the substrate and arranged at a site in contact with the blood flow path of the flexible tube; and
        a planarly wound first coil wound within a plane parallel to a surface of the substrate;
    wherein the first transmission/reception unit is embedded inside the flexible tube so that an upper end portion of the first transmission/reception unit is flush with an inner wall of the blood flow path; and
    wherein the medical instrument defines a guide feature on an outside surface of the flexible tube that indicates an installation position of the first transmission/reception unit.

2. The sensor system according to claim 1, wherein the second transmission/reception unit comprises:
    a planarly wound second coil defining a second winding axis;
    wherein the first coil defines a first winding axis; and
    wherein the first transmission/reception unit and the second transmission/reception unit are arranged so as to be opposed to each other so that the first winding axis of the first coil is substantially parallel to the second winding axis of the second coil.

3. The sensor system according to claim 2, wherein the second transmission/reception unit is configured to supply drive power to the first transmission/reception unit by current induction.

4. The sensor system according to claim 3, wherein the first transmission/reception unit transmits the detection signal of the sensor unit to the second transmission/reception unit as a modulated digital signal by electromagnetic induction.

5. The sensor system according to claim 1:
    wherein the sensor unit is comprised of a pressure sensor that detects a pressure of blood that flows in the blood flow path.

6. A medical device comprising:
    a medical instrument comprising a flexible tube for conveying a blood flow path; and
    a sensor system comprising:
        a first transmission/reception unit incorporated inside the medical instrument and configured to output a detection signal comprising measurement data; and
        a second transmission/reception unit adapted to detachably install to an outside surface of the medical instrument to transmit/receive signals to and from the first transmission/reception unit in a contactless manner;
        wherein the first transmission/reception unit and the second transmission/reception unit are arranged so as to be opposed to each other across the medical instrument and transmit/receive the signals by electromagnetic induction;
        wherein the first transmission/reception unit comprises:
            a substrate;

a sensor unit mounted on the substrate and arranged at a site in contact with the blood flow path of the flexible tube; and a planarly wound first coil wound within a plane parallel to a surface of the substrate;

wherein the first transmission/reception unit is embedded inside the flexible tube so that an upper end portion of the first transmission/reception unit is flush with an inner wall of the blood flow path; and wherein the flexible tube defines a guide feature on an outside surface of the flexible tube that indicates an installation position of the first transmission/reception unit.

7. The medical device according to claim 6, wherein the second transmission/reception unit comprises:

a planarly wound second coil defining a second winding axis;

wherein the first coil defines a first winding axis; and wherein the first transmission/reception unit and the second transmission/reception unit are arranged so as to be opposed to each other so that the first winding axis of the first coil is substantially parallel to the second winding axis of the second coil.

8. The medical device according to claim 7, wherein the second transmission/reception unit is configured to supply drive power to the first transmission/reception unit by current induction.

9. The medical device according to claim 8, wherein the first transmission/reception unit transmits the detection signal of the sensor unit to the second transmission/reception unit as a modulated digital signal by electromagnetic induction.

10. The medical device according to claim 6:

wherein the sensor unit is comprised of a pressure sensor that detects a pressure of blood that flows in the blood flow path.

11. The medical device according to claim 6:

wherein the guide feature is comprised of a recess on an outside surface of the tube.

* * * * *